United States Patent [19]

Falk et al.

[11] Patent Number: 5,585,422
[45] Date of Patent: Dec. 17, 1996

[54] HYBRID S-TRIAZINE LIGHT STABILIZERS SUBSTITUTED BY BENZOTRIAZOLE OR BENZOPHENONE MOIETIES AND COMPOSITIONS STABILIZED THEREWITH

[75] Inventors: Robert A. Falk, New City, N.Y.; Tyler A. Stevenson, Teaneck, N.J.; Gregory R. Coughlin, Poughkeepsie, N.Y.

[73] Assignee: Ciba-Geigy Corporation, Tarrytown, N.Y.

[21] Appl. No.: 530,972

[22] Filed: Sep. 20, 1995

[51] Int. Cl.$^6$ .................... C08K 5/3492; C07D 251/00; C07D 403/00
[52] U.S. Cl. .................... 524/100; 544/211; 544/212; 544/215; 544/218; 544/219
[58] Field of Search ............... 524/91, 100; 544/212, 544/218, 215, 219, 211

[56] References Cited

U.S. PATENT DOCUMENTS

| | | | |
|---|---|---|---|
| 3,004,896 | 10/1961 | Heller et al. | 167/90 |
| 3,055,896 | 9/1962 | Boyle et al. | 260/249.5 |
| 3,072,585 | 1/1963 | Milionis et al. | 260/22 |
| 3,074,910 | 1/1963 | Dickson | 260/45.75 |
| 3,230,194 | 1/1966 | Boyle | 260/45.8 |
| 3,242,175 | 3/1966 | Duennenberg et al. | 260/248 |
| 3,244,708 | 4/1966 | Duennenberger et al. | 260/248 |
| 3,268,474 | 8/1966 | Hardy et al. | 260/45.8 |
| 3,399,237 | 6/1964 | Dressler et al. | 260/591 |
| 3,843,371 | 10/1974 | Piller et al. | 96/84 |
| 3,936,305 | 2/1976 | Hiraishi | 96/84 |
| 4,127,586 | 11/1978 | Rody et al. | 260/308 |
| 4,169,089 | 9/1979 | Minagawa et al. | 260/45.95 |
| 4,226,763 | 10/1980 | Dexter et al. | 260/45.8 |
| 4,278,590 | 7/1981 | Dexter et al. | 260/45.8 |
| 4,283,327 | 8/1981 | Dexter et al. | 260/45.8 |
| 4,315,848 | 2/1982 | Dexter et al. | 260/45.8 |
| 4,355,071 | 10/1982 | Chang | 428/334 |
| 4,383,863 | 5/1983 | Dexter et al. | 106/125 |
| 4,619,956 | 10/1986 | Susi | 524/87 |
| 4,675,352 | 6/1987 | Winter et al. | 524/91 |
| 4,681,905 | 7/1987 | Kubota et al. | 524/91 |
| 4,684,679 | 8/1987 | Kubota et al. | 524/91 |
| 4,740,542 | 4/1988 | Susi | 524/87 |
| 4,826,978 | 5/1989 | Migdal et al. | 544/216 |
| 4,831,068 | 5/1989 | Reinert et al. | 524/100 |
| 4,853,471 | 8/1989 | Rody et al. | 548/261 |
| 4,950,304 | 8/1990 | Reinert et al. | 8/566 |
| 4,962,142 | 10/1990 | Migdal et al. | 524/100 |
| 5,084,570 | 1/1992 | Burdeska et al. | 544/216 |
| 5,096,489 | 3/1992 | Laver | 106/20 |
| 5,108,835 | 9/1992 | Hahnsen et al. | 428/334 |
| 5,166,355 | 11/1992 | Leistner et al. | 548/260 |
| 5,298,030 | 3/1994 | Burdeska et al. | 8/442 |
| 5,298,067 | 3/1994 | Valet et al. | 106/506 |
| 5,300,414 | 4/1994 | Leppard et al. | 430/507 |
| 5,322,868 | 6/1994 | Valet et al. | 524/89 |
| 5,350,449 | 9/1994 | Valet et al. | 106/506 |
| 5,354,794 | 11/1994 | Stevenson et al. | 524/100 |
| 5,364,749 | 11/1994 | Leppard et al. | 430/507 |
| 5,369,140 | 11/1994 | Valet et al. | 522/75 |
| 5,376,710 | 12/1994 | Slengo | 524/87 |

FOREIGN PATENT DOCUMENTS

| | | |
|---|---|---|
| 0165608 | 12/1985 | European Pat. Off. . |
| 0200190 | 11/1986 | European Pat. Off. . |
| 0280653 | 8/1988 | European Pat. Off. . |
| 0431868 | 6/1991 | European Pat. Off. . |
| 0434608 | 6/1991 | European Pat. Off. . |
| 0442847 | 8/1991 | European Pat. Off. . |
| 0444323 | 9/1991 | European Pat. Off. . |
| 0468921 | 1/1992 | European Pat. Off. . |
| 0506615 | 2/1992 | European Pat. Off. . |
| 0483488 | 5/1992 | European Pat. Off. . |
| 0557247 | 8/1993 | European Pat. Off. . |
| 603130 | 6/1994 | European Pat. Off. ............... 544/215 |
| 0613891 | 9/1994 | European Pat. Off. . |
| 0205493 | 9/1994 | European Pat. Off. . |
| 4978692 | 7/1974 | Japan . |
| 5074579 | 6/1975 | Japan . |
| 5086487 | 7/1975 | Japan . |
| 53-113849 | 10/1978 | Japan . |
| 9405645 | 3/1994 | WIPO . |

*Primary Examiner*—Veronica P. Hoke
*Attorney, Agent, or Firm*—Luther A. R. Hall

[57] ABSTRACT s-Triazine UV absorbers substituted by a benzotriazolyl or benzophenonyl moiety exhibit unexpectedly improved UV absorption characteristics and outstanding efficacy in protecting organic substances from the deleterious effects of actinic radiation as well as good resistance to loss by volatilization during processing of stabilized compositions at elevated temperatures.

22 Claims, No Drawings

HYBRID S-TRIAZINE LIGHT STABILIZERS SUBSTITUTED BY BENZOTRIAZOLE OR BENZOPHENONE MOIETIES AND COMPOSITIONS STABILIZED THEREWITH

The instant invention pertains to s-triazine UV absorbers substituted by a benzotriazolyl or benzophenonyl moiety and to compositions of organic materials stabilized therewith.

BACKGROUND OF THE INVENTION

The UV absorbers of the 2H-benzotriazole and benzophenone types have long been known as very effective light stabilizers for a host of organic materials and have enjoyed considerable commercial success. Recently, the long known s-triazine UV absorbers have been shown to exhibit particularly good thermal stability in addition to their light stabilization efficacy.

U.S. Pat. Nos. 3,004,896; 3,055,896; 3,072,585; 3,074,910; 3,230,194; 4,127,586; 4,226,763; 4,278,589; 4,315,848; 4,383,863; 4,675,352; 4,681,905 and 4,853,471 describe the preparation and uses of the 2H-benzotriazole UV absorbers.

The description, preparation and uses of the benzophenone UV absorbers are found in a comprehensive review by G. R. Lapin in the "Encyclopedia of Polymer Science and Technology", N. Bikales, editor, John Wiley-Interscience, New York, Vol. 14, 1971, pp 125–148.

s-Triazine UV absorbers are described in U.S. Pat. Nos. 5,376,710; 5,369,140; 5,364,749; 5,354,794; 5,350,449; 5,322,868; 5,300,414; 5,298,067; 5,298,030; 5,288,778; 5,106,972; 5,106,891; 5,096,489; 5,084,570; 4,962,142; 4,950,304; 4,831,068; 4,826,978; 4,740,542; 4,619,956; 4,355,071 and 3,843,371; as well as copending application Ser. Nos. 08/143,525; 08/281,381; 08/463,140; 08/463,569; 08/463,572 and 08/463,573; and EP 557,247; 506,615; 483,488; 468,921; 444,323; 442,847; 434,608; 280,653; 205,493; 200,190 and 165,608; as well as WO94/05645.

In many instances, the s-triazine, benzotriazole and/or benzophenone UV absorbers exhibit limited compatability with certain substrates and/or an excessive tendency to exude, sublime or volatilize away during processing of stabilized compositions into sheets, films or other pellicles when processing is done at elevated temperatures as described in U.S. Pat. Nos. 3,268,474; 3,244,708; 3,242,175 and 3,188,887. Likewise, such compounds may also suffer undue loss by volatilization or sublimation from fabricated structures, particularly thin films, coatings or fibers, when such structures are subjected to elevated temperatures during use.

Attempts have been made to increase compatibility and/or reduce volatility by modifying the structure of these UV absorbers. Hybrid products of benzophenones and benzotriazoles have been reported and an example of such a UV absorber useful in the range of 240–420 nm is described in EP 431,868, namely 3,5-bis(2H-benzotriazol-2-yl)-2,4,4'-trihydroxybenzophenone.

EP 613,891 teaches that hybrid products such as 2-(benzotriazol-2-yl)-4-alkyl-6-(2-hydroxy-3-benzoyl-6-alkoxybenzyl)phenols are prepared by reacting a Mannich base of 2-(2-hydroxy-5-alkylphenyl)-2H-benzotriazole with a 2-hydroxy-4-alkoxybenzophenone. The hybrid products exhibit outstanding efficacy in protecting organic substrates from light induced deterioration as well as good resistance to loss by volatilization or exudation during process of stabilized compositions at elevated temperatures.

U.S. Pat. No. 3,230,194 teaches that substitution of a higher alkyl group such as tert-octyl for a lower alkyl group such as methyl improves compatibility and performance of substituted benzotriazole UV absorbers in polyethylene.

Likewise, U.S. Pat. Nos. 4,278,590; 4,283,327 and 4,383,863 show that 2-(2-hydroxy-3,5-di-tert-octylphenyl)-2H-benzotriazole exhibits and excellent combination of compatibility with and/or solubility in numerous polymer substrates along with superior resistance to loss from volatilization during high temperature processing, in end-use application where coatings or films of the stabilized compositions are exposed to ambient weathering and actinic light, and in photographic applications.

U.S. Pat. No. 4,675,352 teaches that liquid benzotriazole UV absorbers of low volatility are prepared by the alkylation of preformed 2-(2-hydroxy-5-methylphenyl)-2H-benzotriazole.

U.S. Pat. Nos. 3,936,305; 4,681,905; 4,684; 4,684,679 and 5,108,835 disclose 2,2'-methylene-bis[4-hydrocarbyl-6-(benzotriazol-2-yl)phenols] having high molar activities and low volatility.

U.S. Pat. Nos. 3,399,237 and 4,169,089; Japanese Sho 53-113849; 57-6470; 49-78692; 50-74579 and 50-86487 teach the corresponding class of low volatility compounds with high molar activities which are the methylene-bis(2-hydroxybenzophenones).

U.S. Pat. No. 5,166,355 describes a process for making 2,2'-methylene-bis[6-(2H-benzotriazol-2-yl)-4-hydrocarbylphenol] or 5,5'-methylene-bis(2-hydroxy-4-alkoxy-benzophenone) using bis(dialkylamino)methane.

The instant compounds are structurally distinguished from each of the compounds of the prior art and said instant compounds exhibit decreased volatility and an unexpected enhancement of their absorption characteristics over a particularly broad ultraviolet range. Their photographic inertness is particularly valuable for their use in photographic compositions, especially in protecting color dye images against the harmful effects of actinic light.

OBJECTS OF THE INVENTION

One object of the invention is to provide new hybrid UV absorbers having superior UV absorbing properties and stabilization efficacy.

Another object of the invention is to provide superior stabilized compositions using said compounds particularly in photographic applications.

DETAILED DESCRIPTION

The instant invention pertains to s-triazine UV absorbers substituted by a benzotriazolyl or benzophenonyl moiety and to compositions of organic materials stabilized therewith.

More particularly, the instant invention relates to compounds of formula I or II wherein X and Y are the same or different and are phenyl or phenyl substituted by one to three lower alkyl, halogen, hydroxy or alkoxy, $T_1$ is hydrogen, chloro, alkyl of 1 to 4 carbon atoms or —$SO_3H$, $T_2$ is alkyl of 1 to 12 carbon atoms, $E_1$ is hydrogen, chloro or —$OE_2$, $E_2$ is hydrogen or alkyl of 1 to 18 carbon atoms, $E_3$ is hydrogen, alkyl of 1 to 4 carbon atoms, chloro or —$SO_3H$, $E_4$ is hydrogen, chloro or —$OE_5$, $E_5$ is hydrogen or alkyl of 1 to 18 carbon atoms, $E_6$ is hydrogen, hydroxyl or carboxy, $G_1$ is hydrogen, or when $G_1$ is in the 5-position of the phenyl ring, $G_1$ is also straight or branched alkyl of 1 to 24 carbon atoms, cycloalkyl of 5 to 12 carbon atoms or phenylalkyl of 7 to 15 carbon atoms, R is hydrogen, straight or branched chain alkyl of 1 to 24 carbon atoms or cycloalkyl of 5 to 12 carbon atoms; or said alkyl or cycloalkyl substituted by one to eight halogen, epoxy, glycidyloxy, furyloxy, —$R_2$, —$OR_3$, —$N(R_3)_2$, —$CON(R_3)_2$, —$COR_3$, —$COOR_3$, —$OCOR_3$, —$OCOC(R_3)=C(R_3)_2$, —$C(R_3)=CCOOR_3$, —CN, —NCO, or combinations thereof; or said alkyl or cycloalkyl interrupted by one to six epoxy, —O—, —$NR_3$—, —$CONR_3$—, —COO—, —OCO—, —CO—, —$C(R_3)=C(R_3)COO$—, —$OCOC(R_3)=C(R_3)$—, —$(R_3)C=C(R_3)$—, phenylene, or -phenylene-G-phenylene in which G is —O—, —S—, —$SO_2$—, —$CH_2$—, or —$C(CH_3)_2$—, or combinations thereof; or said alkyl or cycloalkyl both substituted and interrupted by combinations of the groups mentioned above; or R is —$SO_2R_1$, or —$COR_4$;

$R_1$ is alkyl of 1 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms;

$R_2$ is aryl of 6 to 10 carbon atoms, or said aryl substituted by one to three halogen, alkyl of 1 to 8 carbon atoms, alkoxy of 1 to 8 carbon atoms or combinations thereof; cycloalkyl of 5 to 12 carbon atoms; or phenylalkyl of 7 to 15 carbon atoms, or said phenylalkyl substituted on the phenyl ring by one to three halogen, alkyl of 1 to 8 carbon atoms, alkoxy of 1 to 8 carbon atoms or combinations thereof; or straight or branched chain alkenyl of 2 to 18 carbon atoms;

$R_3$ is defined as $R_2$, or $R_3$ is also hydrogen or straight or branched chain alkyl of 1 to 24 carbon atoms; or $R_3$ is a group of the formula where T is hydrogen, oxyl, hydroxyl, alkyl of 1 to 12 carbon atoms, said alkyl substituted by at least one hydroxyl or lower alkoxy, benzyl or alkanoyl of 2 to 18 carbon atoms;

$R_4$ is straight or branched chain alkyl of 1 to 18 carbon atoms, straight or branched chain alkenyl of 2 to 18 carbon atoms, phenyl, alkoxy of 1 to 12 carbon atoms, phenoxy, alkylamino of 1 to 12 carbon atoms, arylamino of 6 to 12 carbon atoms or a group —$R_5COOH$ or —NH—$R_6$—NCO;

$R_5$ is alkylene of 2 to 14 carbon atoms or o-phenylene;

$R_6$ is alkylene of 2 to 10 carbon atoms, phenylene, tolylene, diphenylenemethane or a group Preferably, $T_1$ is hydrogen or chloro; most preferably, hydrogen.

Preferably $T_2$ is alkyl of 1 to 12 carbon atoms; most preferably alkyl of 1 to 8 carbon atoms.

Preferably $E_1$ is —$OE_2$ where $E_2$ is hydrogen or alkyl of 1 to 12 carbon atoms; most preferably where $E_2$ is hydrogen or alkyl of 1 to 8 carbon atoms.

Preferably $E_3$ is hydrogen.

Preferably $E_4$ is hydrogen or —$OE_5$ where $E_5$ is hydrogen or alkyl of 1 to 12 carbon atoms; most preferably where $E_5$ is hydrogen or alkyl of 1 to 4 carbon atoms.

Preferably $E_6$ is hydrogen or hydroxyl.

Especially preferred are the compounds where $T_1$ is hydrogen or chloro, $T_2$ is alkyl of 1 to 12 carbon atoms, $E_1$ is —$OE_2$ where $E_2$ is hydrogen of alkyl of 1 to 12 carbon atoms, $E_3$ is hydrogen, $E_4$ is hydrogen or —$OE_5$ where $E_5$ is hydrogen or alkyl of 1 to 12 carbon atoms, and $E_6$ is hydrogen or hydroxyl.

Still more preferred are the compounds where $T_1$ is hydrogen, $T_2$ is alkyl of 1 to 8 carbon atoms, $E_1$ is —$OE_2$ where $E_2$ is alkyl of 1 to 12 carbon atoms, and each of $E_3$, $E_4$ and $E_6$ is hydrogen.

Preferably, X and Y are phenyl or phenyl substituted with one to three lower alkyl or halogen;

R is straight or branched chain alkyl of 2 to 24 carbon atoms, or said alkyl substituted by one or two —$OR_3$, where $R_3$ is hydrogen, straight or branched chain alkyl of 1 to 24 carbon atoms, or phenyl.

Especially preferred are compounds where R is alkyl of 2 to 24 carbon atoms substituted by one hydroxyl and by one —$OR_3$ where $R_3$ is alkyl of 1 to 24 carbon atoms or phenyl.

Most preferably, X and Y are phenyl, 2,4-dimethylphenyl, 4-methyl phenyl, or 4-chlorophenyl;

R is straight or branched chain alkyl of 2 to 6 carbon atoms, or said alkyl substituted by one or two —$OR_3$ where $R_3$ is hydrogen or straight or branched chain alkyl of 1 to 24 carbon atoms; especially wherein R is alkyl of 1 to 24 carbon substituted by one hydroxyl and by one alkoxy of 1 to 24 carbon atoms.

When any of $T_1$ to $E_6$ is alkyl, such groups are, for example, methyl, ethyl, isopropyl, n-butyl, isobutyl, sec-butyl, tert-butyl, tert-amyl, 2-ethylhexyl, isooctyl, tert-octyl, lauryl, tert-dodecyl, tridecyl, n-hexadecyl and n-octadecyl.

The instant invention also pertains to stabilized compositions which comprise (a) an organic material subject to degradation by the imposition of actinic light, and (b) an effective stabilizing amount of a compound of formula I as described supra.

Preferably the stabilized compositions are those wherein the organic material of component (a) is a synthetic polymer selected from the group consisting of polystyrene, graft copolymers of styrene, polyphenylene oxides, polyphenylene sulfides, polyurethanes, polyureas, polyimides, polyamide-imides, aromatic polyesters, polycarbonates, polysulfones, polyethersulfones, polyetherketones, alkyd resins, aminoplast resins and epoxy resins; or is a polyolefin.

The instant compounds are prepared making a Mannich base of a 2H-benzotriazole having the 3-position on the phenyl ring unoccupied and reacting said Mannich base with a s-triazine; or by making a Mannich base of a s-triazine and reacting said Mannich base with a benzotriazole or a benzophenone. The s-triazines, the benzophenones and said 2H-benzotriazoles are largely items of commerce or can be easily prepared by methods known to those of ordinary skill in the art. The instant compounds can also be made by making a Mannich base of the benzophenone and reacting it with an appropriate s-triazine.

The instant compounds exhibit good resistance to volatilization, have enhanced solubility in selected solvents, have desirable ultraviolet absorption characteristics and are photographically inert. This combination of properties makes them particularly useful in photographic compositions especially in protecting color dye images against the harmful effects of ultraviolet light.

The instant compounds are useful as ultraviolet absorbers in photographic gelatin layers. The compounds show maximum absorption in the near ultraviolet and sharp cut-off just outside the visible region. The compounds are essentially colorless, are readily dispersed or dissolved by either solvent-dispersion or imbibition methods and are photographically inert.

The instant compounds exhibit excellent compatibility characteristics in the gelatin layers of the photographic composition which lead to compositions essentially without haze coupled with superior protection of the color dye images against the harmful effects of ultraviolet radiation. This combination of properties clearly distinguishes the instant compounds over the closest compounds of the prior art.

Preferably the organic material is a synthetic polymer. Such polymers are especially those containing aromatic moieties such as polystyrene, graft copolymers of styrene such as ABS resins, polyphenylene oxides, polyphenylene sulfides, polyurethanes, polyureas, polyimides, polyamide-imides, aromatic polyesters, polycarbonates, polysulfones, polyethersulfones, polyetherketones, alkyd resins, aminoplast resins and epoxy resins.

Another class of synthetic polymers of especial importance are the polyolefins, such as polypropylene.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(α-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, /isoprene/styrene, /ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxy resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols, for example, 2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example, 2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example, 2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example, 2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.

1.5. Benzyl compounds, for example, 1,3,5-tri-(3,5-di-tert-butyl-4-hydroxybenzyl)-2,4,6-trimethylbenzene
di-(3,5-di-tert-butyl-4-hydroxybenzyl)sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example, 4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example, N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), di-(1-octyloxy-2,2,6,6-tetramethylpiperidin-4-yl) sebacate, di-(1-cyclohexyloxy-2,2,6,6-tetramethylpiperidin-4-yl)succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], 2,4,6-tris[N-(1-cyclohexyloxy-2,2,6,6-tetramethylpiperidin-4-yl)-n-butylamino]-s-triazine.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alphaheptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate ), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl- 4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl- 4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-tri-methyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidenebis(4,6-di-tert-butylphenol).

The hindered amine compound of particular interest is selected from the group consisting of bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl)nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/β,tetramethyl-3,9-(2,4,8,10-tetraoxaspiro[5.5]-undecane) diethyl]1,2,3,4-butanetetracarboxylate, mixed [1,2,2,6,6-pentamethylpiperidin-4-yl/β,tetramethyl-3,9-(2,4,8,10-tetraoxaspiro[5.5]-undecane)diethyl]1,2,3,4-butanetetracarboxylate, octamethylene bis(2,2,6,6-tetramethylpiperidin- 4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yln-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], and 2,4,6-tris[N-(1-cyclohexyloxy-2,2,6,6-tetramethylpiperidin-4-yl)-n-butylamino]-s-triazine.

A most preferred hindered amine compound is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]-1,10-diamino-4,7-diazadecane. di-(1-octyloxy-2,2,6,6-tetramethylpiperidin-4-yl)sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], or 2,4,6-tris[N-(1-cyclohexyloxy-2,2,6,6-tetramethylpiperidin-4-yl)-n-butylamino]-s-triazine.

The following examples are presented for the purpose of illustration only and are not to be construed to limit the nature or scope of the instant invention in any manner whatsoever.

EXAMPLE 1

2-(2-Hydroxy-3-diethylaminomethyl-5-methylphenyl)-2H-benzotriazole 2-(2-Hydroxy-5-methylphenyl)-2H-benzotriazole (74.3 g, 0.33 mol), diethylamine (37.0 g, 0.51 mol) and paraformaldehyde (17.1 g) are dissolved in 85 mL of n-butanol. The mixture is heated with agitation at reflux (95° to 100° C.) for 44 hours. The solvent is then removed by vacuum distillation to give a yellow viscous liquid as product in high yield (>99%). This Mannich base is identified as the above-named compound by thin layer chromatography using toluene as the mobile phase.

EXAMPLE 2

2-(2-Hydroxy-3-diethylaminomethyl-5-tert-octylphenyl)-2H-benzotriazole 2-(2-Hydroxy-5-tert-octylphenyl)-2H-benzotriazole (70.0 g, 0.22 mol), diethylamine (24.3 g, 0.33 mol) and paraformaldehyde (11.2 g) are dissolved in 55 mL of n-butanol. The mixture is heated with agitation at reflux (95° to 100° C.) for 50 hours. The solvent is then removed by vacuum distillation to give an off-white solid as product in high yield (>99%). This Mannich base is identified as the above-named compound by thin layer chromatography using toluene as the mobile phase.

EXAMPLE 3

2,4-Diphenyl-6-(2-hydroxy-3-piperidinomethyl-4-hexyloxyphenyl)-s-triazine and

2,4-Diphenyl-6-(2-hydroxy-5-piperidinomethyl-4-hexyloxyphenyl)-s-triazine 2,4-Diphenyl-6-(2-hydroxy-4-hexyloxyphenyl)-s-triazine (42.5 g, 0.1 mol), dipiperidinomethane (17.5 g, 0.096 mol) and sodium hydroxide (0.8 g, 0.02 mol) are dissolved in 42 g of mesitylene. The mixture is heated with agitation at 160° C. for 18 hours. Acetic acid (8.5 g) is then added and the reaction mixture is heated for 30 minutes at 120°–130° C. Toluene (300 ml) is added and the heating is continued till the reaction product dissolves. The reaction mixture is then cooled to room temperature and the product crystallizes to give 21 g of reaction product. The crude product is recrystallized from 500 ml of toluene to yield 15 g of final product.

Thin layer chromatography using toluene/methanol 5/1 as the mobile phase gives predominantly one component. The product is identified as a 9/1 mixture of isomeric 3- and 5-piperidinomethyl Mannich bases by proton $^1$H NMR. The product is an off-white solid melting at 190°–192° C.

$^1$H NMR shows proton resonances consistent with two isomeric mono-substituted compounds with an isomer ratio of 9/1 for the 3-substituted versus the 5-substituted isomers. A major "ortho" doublet is seen at 6.64 ppm and a minor isomer "para" singlet at 6.53 ppm. Mass spectral data is determined by EI and DCI spectrometry. A parent peak is found at m/z=522 and fragment peaks at m/z=439, 438, 368, 148, 104 and 84, consistent with the structural assignment for the title mixture.

The two isomeric products can be separated by conventional organic techniques although the mixture itself can be used acceptably as a starting material for making the instant compounds.

EXAMPLE 4

2,2'-Dihydroxy-3-(2H-benzotriazol-2-yl)-3'-(4,6-diphenyl-s-triazin-2-yl)-5-methyl-6'-hexyloxyoxy-diphenylmethane 2,4-Diphenyl-6-(2-hydroxy-3-piperidinomethyl-4-hexyloxyphenyl)-s-triazine (5.2 g, 0.01 mol, as prepared in Example 3), 2-(2-hydroxy-5-methylphenyl)-2H-benzotriazole (2.5 g, 0.011 mol) and sodium methylate (1.0 g, 21% in methanol) are dissolved in 80 g of mesitylene. The reaction mixture is heated with agitation at 160°–180° C. for 24 hours. The disappearance of the starting benzotriazole and appearance of product is followed by thin layer chromatography on silica gel plates with toluene/methanol 9/1 as eluant. Acetic acid (8.5 g) is then added and followed by sufficient toluene to allow for hot filtration. The reaction product is crystallized with the assistance of added methanol and cooling. The crude crystalline product (4 grams) is isolated by filtration, dissolved in hot toluene, treated with silica gel to remove colored impurities, and isolated by filtration to give a single yellow solid product which after drying under vacuum melts at 188°–189° C.

$^1$H NMR, NOE and decoupling experiments on the product in CDCl$_3$ at ambient temperature suggest a single material with very minor impurities and are consistent with the structure of the title compound.

Analysis: Calcd for $C_{41}H_{38}N_6O_3$: C, 74.3; H, 5.8; N, 12.7. Found: C, 73.7; H, 5.5; N, 12.2.

EXAMPLE 5

2,2'-Dihydroxy-3-(2H-benzotriazol-2-yl)-3'-(4,6-diphenyl-s-triazin-2-yl)-5-tert-octyl-6'-hexyloxy-diphenylmethane 2,4-Diphenyl-6-(2-hydroxy-3-piperidinomethyl-4-hexyloxyphenyl)-s-triazine (2.6 g, 0.005 mol, as prepared in Example 3), 2-(2-hydroxy-5-tert-octylphenyl)-2H-benzotriazole (1.78 g, 0.0055 mol) and sodium methylate (0.5 g, 21% in methanol) are dissolved in 50 g of tetralin. The reaction mixture is heated with agitation at 160°–174° C. for 24 hours. The disappearance of the starting benzotriazole and appearance of product is followed by thin layer chromatography on silica gel plates with heptane/methanol 10/1. Additional benzotriazole (0.2 g) is added and the reaction mixture heated for an additional 22 hours. Acetic acid (1.0 g) is then added and the reaction mixture is chromatographed on silica gel with toluene as eluant. The second fraction is vacuum dried to give the product as a single yellow solid melting at 85°–87° C.

$^1$H NMR experiments on the product in CDCl$_3$ at ambient temperature suggest a single material with very minor impurities including tetralin and is consistent with the structure of the title compound.

Analysis: Calcd for $C_{48}H_{52}N_6O_3$: C, 75.7; H, 6.9; N, 11.0. Found: C, 75.6; H, 7.1; N, 10.3.

EXAMPLES 6–12

Following the general procedure of Examples 4 and 5 using the Mannich intermediates of Examples 1–3, the following hybrid UV absorbers containing s-triazinyl and benzotriazolyl moieties are prepared as seen in the Table below.

(A)

| Example | T$_1$ | T$_2$ | R | G$_1$ | X | Y |
|---|---|---|---|---|---|---|
| 6 | H | methyl | hexyl | H | xylyl | xylyl |
| 7 | Cl | methyl | octyl | H | phenyl | phenyl |
| 8 | H | t-octyl | octyl | α-cumyl | xylyl | xylyl |
| 9 | H | t-octyl | hexyl | H | tolyl | tolyl |
| 10 | H | methyl | octyl | H | xylyl | xylyl |
| 11 | H | t-octyl | dodecyl | H | phenyl | phenyl |
| 12 | Cl | methyl | nonyl | H | xylyl | xylyl |

EXAMPLES 13–19

Following the general procedure of Examples 4 and 5 using the Mannich intermediates of Examples 1–3, the following hybrid UV absorbers containing s-triazinyl and benzophenonyl moieties are prepared as seen in the Table below.

(B)

| Example | E$_1$ | E$_3$ | E$_4$ | E$_6$ | R | X | Y |
|---|---|---|---|---|---|---|---|
| 13 | octyloxy | H | H | H | hexyl | phenyl | phenyl |
| 14 | methoxy | H | H | H | octyl | phenyl | phenyl |
| 15 | octyloxy | H | H | H | nonyl | xylyl | xylyl |

-continued

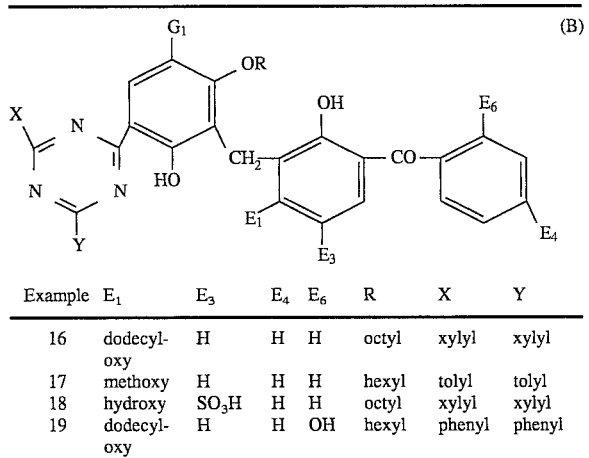

| Example | $E_1$ | $E_3$ | $E_4$ | $E_6$ | R | X | Y |
|---|---|---|---|---|---|---|---|
| 16 | dodecyloxy | H | H | H | octyl | xylyl | xylyl |
| 17 | methoxy | H | H | H | hexyl | tolyl | tolyl |
| 18 | hydroxy | $SO_3H$ | H | H | octyl | xylyl | xylyl |
| 19 | dodecyloxy | H | H | OH | hexyl | phenyl | phenyl |

$G_1$ is hydrogen in each of Examples 13–19.

EXAMPLE 20

Delamination Resistance of High Solids Thermoset Acrylic Clear Coats Containing UV Absorbers Applied over UV Transparent Base Coats Test panels are prepared by spray applying a 1.8–2.0 mil (0.036–0.051 mm) thick film of a commercially available high solids thermoset acrylic melamine clear coat, containing 2% by weight, based on the acrylic melamine resin, of a test UV absorber stabilizer of this invention, over a commercially available UV transparent base coat, wet-on-wet. The topcoat is applied over 4"×12" (10.16 cm×30.48 cm) UNIPRIME® panels obtained from Advance Coatings Technology, Inc. The coated panels are then baked at 250° F. (121° C.) for 30 minutes. After storage for one week in an air-conditioned room, the panels are exposed in Florida at 5° South, black box according to SAE J-1976. The panels are exposed for one year. After one year, a humidity test is conducted consisting of exposing the panels to 100° F. (38° C.) and 100% humidity for four days. After four days, a tape adhesion test is performed.

The instant compounds are effective in improving adhesion of the clear coat to the base coat during weathering.

EXAMPLE 21

Delamination Resistance of Acrylic Urethane Clear Coats Containing UV Absorbers Applied Directly over Electrocoat Primer Test panels are prepared by spray applying a 1.8–2.0 mil (0.036–0.051 mm) thick film of a commercially available acrylic urethane clear coat, containing 2% by weight, based on the acrylic urethane resin, of a test UV absorber stabilizer of this invention, directly over 4"×12" (10.16 cm×30.48 cm) UNIPRIME® panels obtained from Advance Coatings Technology, Inc. The coated panels are then baked at 250° F. (121° C.) for 30 minutes. After storage for one week in an air-conditioned room, the panels are exposed in Florida at 5° South, black box according to SAE J-1976. The panels are evaluated every day for delamination and are retired from the test when delamination is evident over 10% of the panel area.

The instant compounds are effective in delaying delamination of the clear coat from the electrocoat primer.

EXAMPLE 22

The following example demonstrates the utility of the o-hydroxyphenyl-s-triazines of the instant invention in a laminated polycarbonate plaque wherein the UV absorber is incorporated only into the thin surface protecting layer such as prepared in a coextruded article.

Laminated plaques are prepared by bonding a 1 mil (0.0254 mm) polycarbonate film (LEXAN® 141-111N, General Electric Co.) containing 5% by weight of an UV absorber to a non-UV stabilized 125 mil (3.18 mm) polycarbonate plaque (LEXAN® 141-111N) via compression molding in a Wabash Compression molder at 350° F. (177° C.) for three minutes at 1000 psi (70 Kg/cm²), three minutes at 3000 psi (210 Kg/cm²), and then three minutes at 3000 psi (210 Kg/cm²) while cooling. The plaques are then exposed in an Atlas CI-65 Xenon Arc Weatherometer, using the ASTM designation G26-88 Test Method C with the protective layer facing the incident light. Polymer degradation is determined by measuring yellowness index (YI) on an ACS spectrophotometer.

The hybrid o-hydroxyphenyl-s-triazines of the instant invention are very effective in protecting the polycarbonate sheet from degradation and discoloration.

What is claimed is:

1. A compound of formula I or II

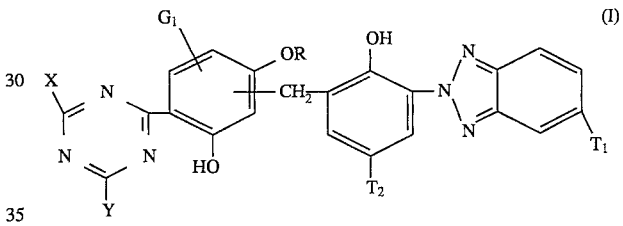

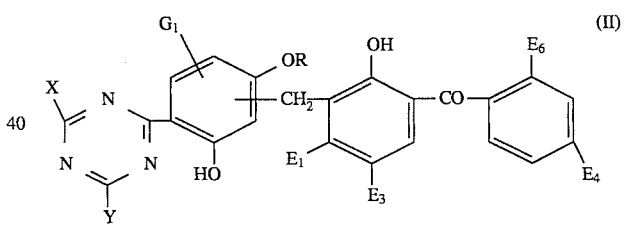

wherein

X and Y are the same or different and are phenyl or phenyl substituted by one to three lower alkyl, halogen, hydroxy or alkoxy, $T_1$ is hydrogen, chloro, alkyl of 1 to 4 carbon atoms or —$SO_3H$, $T_2$ is alkyl of 1 to 12 carbon atoms, $E_1$ is hydrogen, chloro or —$OE_2$, $E_2$ is hydrogen or alkyl of 1 to 18 carbon atoms, $E_3$ is hydrogen, alkyl of 1 to 4 carbon atoms, chloro or —$SO_3H$, $E_4$ is hydrogen, chloro or —$OE_5$, $E_5$ is hydrogen or alkyl of 1 to 18 carbon atoms, $E_6$ is hydrogen, hydroxyl or carboxy, $G_1$ is hydrogen, or when $G_1$ is in the 5-position of the phenyl ring, $G_1$ is also straight or branched alkyl of 1 to 24 carbon atoms, cycloalkyl of 5 to 12 carbon atoms or phenylalkyl of 7 to 15 carbon atoms, R is hydrogen, straight or branched chain alkyl of 1 to 24 carbon atoms or cycloalkyl of 5 to 12 carbon atoms; or said alkyl or cycloalkyl substituted by one to eight halogen, epoxy, glycidyloxy, furyloxy, —R$_2$, —OR$_3$, —N(R$_3$)$_2$, —CON(R$_3$)$_2$, —COR$_3$, —COOR$_3$, —OCOR$_3$, —OCOC(R$_3$)=C(R$_3$)$_2$, —C(R$_3$)=CCOOR$_3$, —CN, —NCO, or

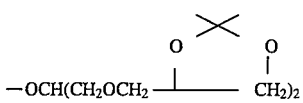

combinations thereof; or said alkyl or cycloalkyl interrupted by one to six epoxy, —O—, —NR$_3$—, —CONR$_3$—, —COO—, —OCO—, —CO—, —C(R$_3$)=C(R$_3$)COO—, —OCOC(R$_3$)=C(R$_3$)—, —(R$_3$)C=C(R$_3$)—, phenylene, or -phenylene-G-phenylene in which G is —O—, —S—, —SO$_2$—, —CH$_2$—, or —C(CH$_3$)$_2$—, or combinations thereof; or said alkyl or cycloalkyl both substituted and interrupted by combinations of the groups mentioned above; or R is —SO$_2$R$_1$, or —COR$_4$;

R$_1$ is alkyl of 1 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms;

R$_2$ is aryl of 6 to 10 carbon atoms, or said aryl substituted by one to three halogen, alkyl of 1 to 8 carbon atoms, alkoxy of 1 to 8 carbon atoms or combinations thereof; cycloalkyl of 5 to 12 carbon atoms; or phenylalkyl of 7 to 15 carbon atoms, or said phenylalkyl substituted on the phenyl ring by one to three halogen, alkyl of 1 to 8 carbon atoms, alkoxy of 1 to 8 carbon atoms or combinations thereof; or straight or branched chain alkenyl of 2 to 18 carbon atoms;

R$_3$ is defined as R$_2$, or R$_3$ is also hydrogen or straight or branched chain alkyl of 1 to 24 carbon atoms; or R$_3$ is a group of the formula

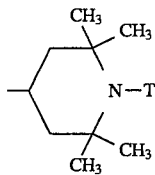

where T is hydrogen, oxyl, hydroxyl, alkyl of 1 to 12 carbon atoms, said alkyl substituted by at least one hydroxyl or lower alkoxy, benzyl or alkanoyl of 2 to 18 carbon atoms;

R$_4$ is straight or branched chain alkyl of 1 to 18 carbon atoms, straight or branched chain alkenyl of 2 to 18 carbon atoms, phenyl, alkoxy of 1 to 12 carbon atoms, phenoxy, alkylamino of 1 to 12 carbon atoms, arylamino of 6 to 12 carbon atoms or a group —R$_5$ COOH or —NH—R$_6$—NCO;

R$_5$ is alkylene of 2 to 14 carbon atoms or o-phenylene; and

R$_6$ is alkylene of 2 to 10 carbon atoms, phenylene, tolylene, diphenylenemethane or a group

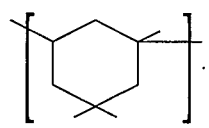

2. A compound according to claim 1 wherein T$_1$ is hydrogen or chloro.

3. A compound according to claim 2 wherein T$_1$ is hydrogen.

4. A compound according to claim 1 wherein T$_2$ is alkyl of 1 to 12 carbon atoms.

5. A compound according to claim 4 wherein T$_2$ is alkyl of 1 to 8 carbon atoms.

6. A compound according to claim 1 wherein E$_1$ is —OE$_2$ where E$_2$ is hydrogen or alkyl of 1 to 12 carbon atoms.

7. A compound according to claim 6 wherein E$_1$ is —OE$_2$ where E$_2$ is hydrogen or alkyl of 1 to 8 carbon atoms.

8. A compound according to claim 1 wherein E$_3$ is hydrogen.

9. A compound according to claim 1 wherein E$_4$ is hydrogen or —OE$_5$ where E$_5$ is hydrogen or alkyl of 1 to 12 carbon atoms.

10. A compound according to claim 9 wherein E$_4$ is —OE$_5$ where E$_5$ is hydrogen or alkyl of 1 to 4 carbon atoms.

11. A compound according to claim 1 wherein E$_6$ is hydrogen or hydroxyl.

12. A compound according to claim 1 wherein T$_1$ is hydrogen or chloro and T$_2$ is alkyl of 1 to 12 carbon atoms; or E$_1$ is —OE$_2$ where E$_2$ is hydrogen of alkyl of 1 to 12 carbon atoms, E$_3$ is hydrogen, E$_4$ is hydrogen or —OE$_5$ where E$_5$ is hydrogen or alkyl of 1 to 12 carbon atoms, and E$_6$ is hydrogen or hydroxyl.

13. A compound according to claim 1 wherein T$_1$ is hydrogen or T$_2$ is alkyl of 1 to 8 carbon atoms; or E$_1$ is —OE$_2$ where E$_2$ is alkyl of 1 to 12 carbon atoms, and each of E$_3$, E$_4$ and E$_6$ is hydrogen.

14. A compound according to claim 1 wherein X and Y are phenyl or phenyl substituted with one to three lower alkyl or halogen; and R is straight or branched chain alkyl of 2 to 24 carbon atoms, or said alkyl substituted by one or two —OR$_3$, where R$_3$ is hydrogen, straight or branched chain alkyl of 1 to 24 carbon atoms, or phenyl.

15. A compound according to claim 1 wherein R is alkyl of 2 to 24 carbon atoms substituted by one hydroxyl and by one —OR$_3$ where R$_3$ is alkyl of 1 to 24 carbon atoms or phenyl.

16. A compound according to claim 1 wherein X and Y are phenyl, 2,4-dimethylphenyl, 4-methyl phenyl, or 4-chlorophenyl;

R is straight or branched chain alkyl of 2 to 6 carbon atoms, or said alkyl substituted by one or two —OR$_3$ where R$_3$ is hydrogen or straight or branched chain alkyl of 1 to 24 carbon atoms.

17. A compound according to claim 16 wherein R is alkyl of 1 to 24 carbon substituted by one hydroxyl and by one alkoxy of 1 to 24 carbon atoms.

18. A compound according to claim 1 which is a. 2,2'-dihydroxy-3-(2H-benzotriazol-2-yl)-3'-(4,6-diphenyl-s-triazin-2-yl)-5-methyl-6'-hexyloxy-diphenylmethane; or b. 2,2'-dihydroxy-3-(2H-benzotriazol-2-yl)-3'-(4,6-diphenyl-s-triazin-2-yl)-5-tert-octyl-6'-hexyloxy-diphenylmethane.

19. A stabilized compositions which comprise (a) an organic material subject to degradation by the imposition of actinic light, and (b) an effective stabilizing amount of a compound of formula I or II according to claim 1.

20. A composition according to claim 19 wherein the organic material of component (a) is a synthetic polymer selected from the group consisting of polystyrene, graft copolymers of styrene, polyphenylene oxides, polyphenylene sulfides, polyurethanes, polyureas, polyimides, polyamide-imides, aromatic polyesters, polycarbonates, polysulfones, polyethersulfones, polyetherketones, alkyd resins, aminoplast resins and epoxy resins.

21. A composition according to claim 19 wherein the organic material of component (a) is a polyolefin.

22. A composition according to claim 19 wherein the compound of component (b) is a. 2,2'-dihydroxy-3-(2H-benzotriazol-2-yl)-3'-(4,6-diphenyl-s-triazin-2-yl)-5-methyl-6'-hexyloxy-diphenylmethane; or
b. 2,2'-dihydroxy-3-(2H-benzotriazol-2-yl)-3'-(4,6-diphenyl-s-triazin-2-yl)-5-tert-octyl-6'-hexyloxy-diphenylmethane.

* * * * *